United States Patent [19]

Jiskoot

[11] Patent Number: 4,470,316
[45] Date of Patent: Sep. 11, 1984

[54] APPARATUS AND METHOD FOR WITHDRAWING FLUID FROM A SOURCE OF FLUID SUCH AS A PIPELINE

[76] Inventor: Jakob J. Jiskoot, 85 Goods Station Rd., Tunbridge Wells, Kent, England

[21] Appl. No.: 313,620

[22] Filed: Oct. 21, 1981

[30] Foreign Application Priority Data

Oct. 21, 1980 [GB] United Kingdom ................. 8033965

[51] Int. Cl.³ ............................................. G01N 1/10
[52] U.S. Cl. .............................. 73/863.84; 73/863.31; 73/864.34; 366/137; 366/140; 222/249
[58] Field of Search ........... 73/863.83, 863.84, 864.34, 73/864.83, 863.31, 863.33; 366/136, 137, 140, 150, 177, 161; 222/249, 250, 253; 422/81; 436/52

[56] References Cited

U.S. PATENT DOCUMENTS

| 2,284,560 | 5/1942 | Corneil | 73/864.61 |
| 2,636,387 | 4/1953 | McKinney et al. | 73/864.34 |
| 3,827,302 | 8/1974 | Sato | 73/863.33 |
| 4,070,913 | 1/1978 | Roof | 73/864.83 X |
| 4,171,191 | 10/1979 | Krueger | 366/161 X |
| 4,299,501 | 11/1981 | Patil et al. | 366/136 X |
| 4,347,223 | 8/1982 | Kitaoka et al. | 222/249 |

FOREIGN PATENT DOCUMENTS

2052055  1/1981  United Kingdom ............. 73/864.34

Primary Examiner—Gerald Goldberg
Assistant Examiner—John E. Chapman, Jr.
Attorney, Agent, or Firm—Staas & Halsey

[57] ABSTRACT

An apparatus and method for withdrawing fluid such as oil from an oil pipeline comprising 2 collection apparatus, an alternate one of which is at all times connected to the pipeline connecting oil, whereby while one is collecting oil, the oil in the other collection apparatus is being mixed and then is emptied ready to receive oil.

13 Claims, 10 Drawing Figures

APPARATUS AND METHOD FOR WITHDRAWING FLUID FROM A SOURCE OF FLUID SUCH AS A PIPELINE

BACKGROUND OF THE INVENTION

The present application relates to apparatus and method for withdrawing fluid from a source of fluid such as a pipeline. In preferred arrangements to be described, the apparatus and method is utilised to withdraw oil from an oil pipeline.

The preferred apparatus and method provides means whereby a small quantity of oil may be withdrawn for sampling purposes from an oil pipeline. There have in the past been many problems associated with withdrawal of such small quantities of oil from a pipeline for analysis. For example, it is only necessary to withdraw a few liters in a twenty four hour period from a pipeline which may be passing tens of thousands of tons of oil during that period.

Generally the sampling of the oil is arranged by taking many small grabs of oil over the period of interest and, for example, it has been suggested that one might require ten thousand grabs over a twenty hour period to produce a ten to fifteen liter sample volume so each grab should be 1 to 1.5 cc taken every 7.2 seconds, which might mean that a sample of water was missed.

The mechanical constraints to achieve this reliably and accurately are very considerable. A further difficulty is that it is preferred to withdraw the sample fluid from the pipeline isokinetically, that is, the velocity of the sample passing up the sample pipe should be the same as the velocity of the oil through the pipeline. If a very small quantity of oil is to be taken then this necessitates the use of a very narrow sampling pipe which can clog.

SUMMARY OF THE INVENTION

The present invention provides apparatus for withdrawing a fluid from a source of fluid, comprising two collection apparatus operable alternately to collect part of the fluid, fluid mixing means connectable alternately to the two collection apparatus to mix the fluid collected in one of the collection apparatus whilst the other collection apparatus is connected to collect fluid, and means for sampling a predetermined quantity of this mixed fluid.

Preferably each collection apparatus comprises a substantially identical vessel having a movable wall means. The vessels may be generally cylindrical and the movable wall means in this case will comprise a ball sealingly engaging the cylindrical inner wall of the respective vessel. Preferably the apparatus includes means to alternately connect pump means to one end of each vessel, the opposite end of each vessel being connectable to the source of fluid so that operation of the pump means withdraws fluid from each vessel alternately whereby the movable wall means is moved within that vessel, and fluid from the source of fluid is thereby withdrawn from the source of fluid to that vessel. Alternatively, pump means is provided to pump fluid from the source of fluid and means is provided to pass pumped fluid to the vessels alternately.

In either case the pump means is preferably a controlled metering pump.

The fluid mixing means may comprise a pump means to withdraw fluid from said one of the collection apparatus and pass said fluid through a mixer. The fluid withdrawn by the fluid mixing means is preferably passed through said one of the collection apparatus so that the fluid is passed through the collection apparatus during mixing.

Withdrawal means may be provided to connect said apparatus to said source of fluid, said withdrawal means being connected to valve means to connect said withdrawal means alternately to said two connection apparatus, second valve means being provided to selectively connect alternately said two collection apparatus to the fluid mixing means, and third valve apparatus arranged to alternately connect said two collection apparatus to means for returning said fluid to the source of fluid.

The present invention also provides a method for withdrawing a fluid from a fluid supply comprising:
alternately withdrawing the fluid to two separate containers,
and whilst one container is being filled, mixing the fluid in the second container, and,
sampling the mixed fluid.

The fluid is preferably mixed by withdrawing from said second container and passing said fluid through a mixer and then returning said fluid to said second container.

Fluid is preferably withdrawn from the fluid supply isokinetically and is pumped into said containers alternately.

The invention also provides for an oil pipeline apparatus for continuously withdrawing oil from the pipeline comprising withdrawal means, a first and second collection apparatus operable alternately to collect a proportion of the oil flow through the pipeline, fluid mixing means connectable alternately to the two collection apparatus to mix the fluid collected in one of the collection apparatus whilst the other collection apparatus is collecting oil from the pipeline and means for sampling a predetermined quantity of the mixed oil, and means for returning the remainder of the mixed oil to the pipeline.

BRIEF DESCRIPTION OF THE DRAWINGS

Preferred arrangements of the invention will now be described by way of example only and with reference to the accompanying drawings.

DETAILED DESCRIPTION OF THE INVENTION

Figure 1:
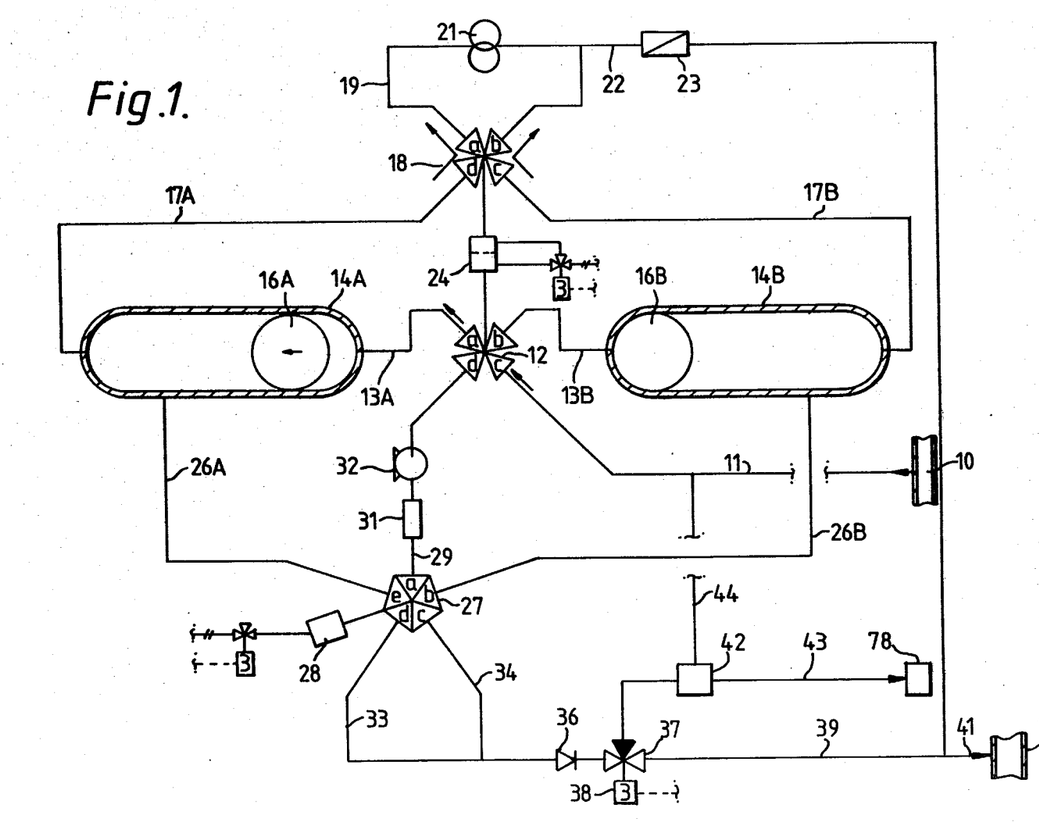
FIGS. 1 to 5 show a first embodiment of the apparatus of the invention in diagramatic form at various stages through the method of the invention.

In the drawings the apparatus comprises an inlet line 11 from a probe inlet which passes into an oil pipeline 10 from which oil is to be withdrawn to a sampler 78. The inlet line 11 passes to port C of a valve 12 which in FIG. 1 is arranged so as to connect the inlet line 11 via port A and a pipeline 13A with a first pressure vessel 14A of, for example, 30 liter capacity. As can be seen the vessel 14A is generally cylindrical and contains therewithin a movable wall member in the form of a ball 16A (which may be of the type referred to in the oil industry as a pig) which is in sealing connection with the inner walls of the vessel 14A. As can be seen the line 13A is connected to the vessel 14A at one end.

A further line 17A is connected with the vessel 14A at the end opposite the line 13A and this line 17A passes to port D of a second valve 18 arranged in FIG. 1 so as to connect line 17A via a port A and a line 19 with a variable speed gear pump 21. The downstream side of the gear pump 21 is connected to line 22 and filter 23.

The valves 12 and 18 are of generally similar construction having four ports labelled A, B, C, D and the valve mechanisms may be rotated by means of an actuator 24 in synchronism with one another so as to cause different ports to be connected to one another as is shown in the Figures. Thus, for example, in FIG. 1 in respect of valve 12, port A is connected to port C and in respect of valve 18 port D is connected to port A and port C is connected to port B.

As is clear from the Figure there is provided a second pressure vessel 14B corresponding to vessel 14A and including ball 16B, the vessel 14B being connected to lines 13B and 17B corresponding to lines 13A and 17A. In FIG. 1 the line 17B is connected through port C of valve 18 to port B and line 22.

Each vessel 14A, 14B is also connected to respective lines 26A, 26B which are connected to respective ports E, B of a valve 27 operated by an actuator 28. The lines 26A, 26B are arranged adjacent the end of the vessel 14A, 14B including the line 17A, 17B in such a position that when the ball 16A, 16B is at that end the line 26A, 26B is in communication with the line 13A, 13B through the vessel 14A, 14B. Port A of the five port valve 27 is connected by line 29 via a mixer 31 and high capacity positive displacement pump 32 to the port D of the valve 12, and ports D, C, by lines 33, 34 via a one way valve 36 to a sampling valve 37. The solenoid operated sampling valve 37 which is operated by an actuator 38 connects the lines 33 and 34 either with line 39 which is in turn connected to a probe return 41 or with a back pressure regulator 42. The back pressure regulator 42 is connected with a line 43 which is an output line for a sample to the sampler 78. There is a further line connection 44 between the probe inlet line 11 and the back pressure regulator 42.

The apparatus thus far described is operated in the following manner. Referring firstly to FIG. 1, as has already been described, line 11 is connected through valve 12 to line 13A, line 17A connected through valve 18 to line 19 and line 17B connected through valve 18 to line 22. The gear pump 21 is driven and this withdraws fluid from the vessel 14A via the line 17A so that the ball 16A is urged to the left. This causes fluid from the pipeline to be withdrawn through the probe inlet line 11 via the valve 12 and line 13A. Thus the vessel 14A to the right of the ball 16A begins to fill with oil from the pipeline. The pump 21 is driven at such a speed that the oil is withdrawn through the probe from the oil pipeline isokinetically, that is, the oil flow through the probe inlet is at exactly the same speed as the oil flow through the pipeline.

Figure 2:
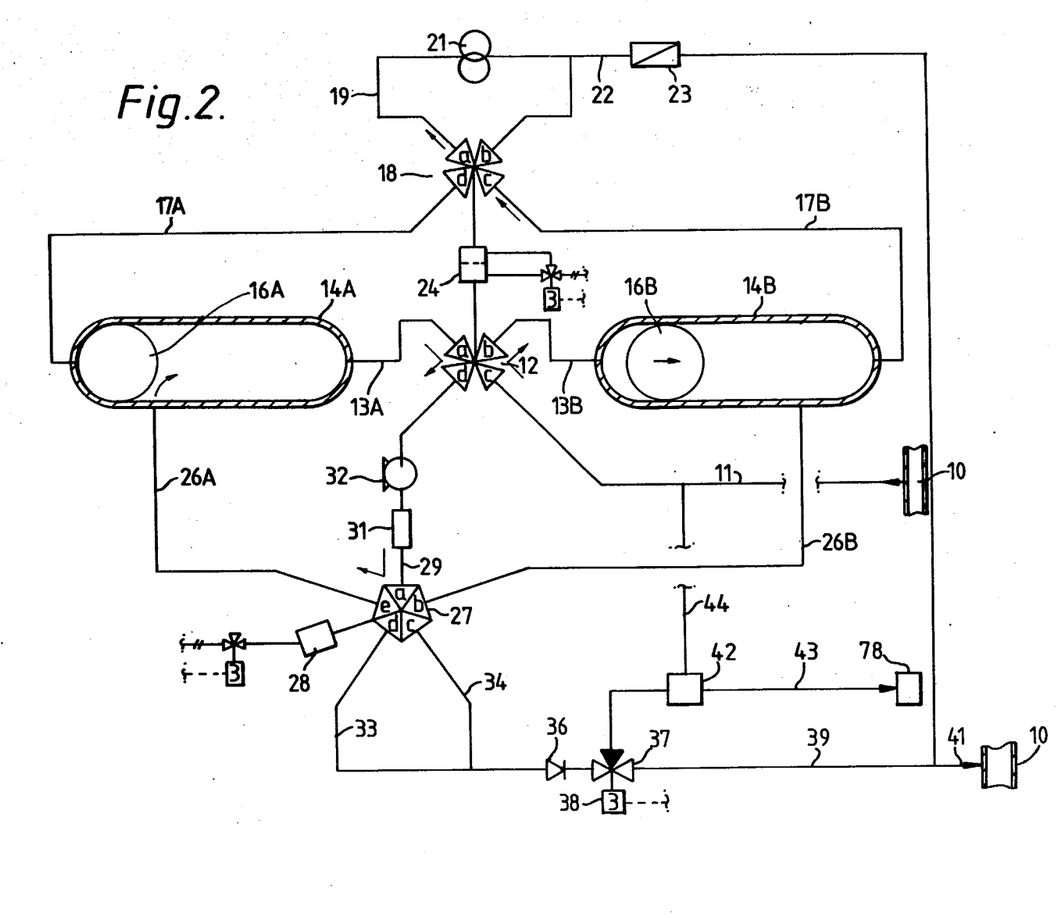
Figure 3:
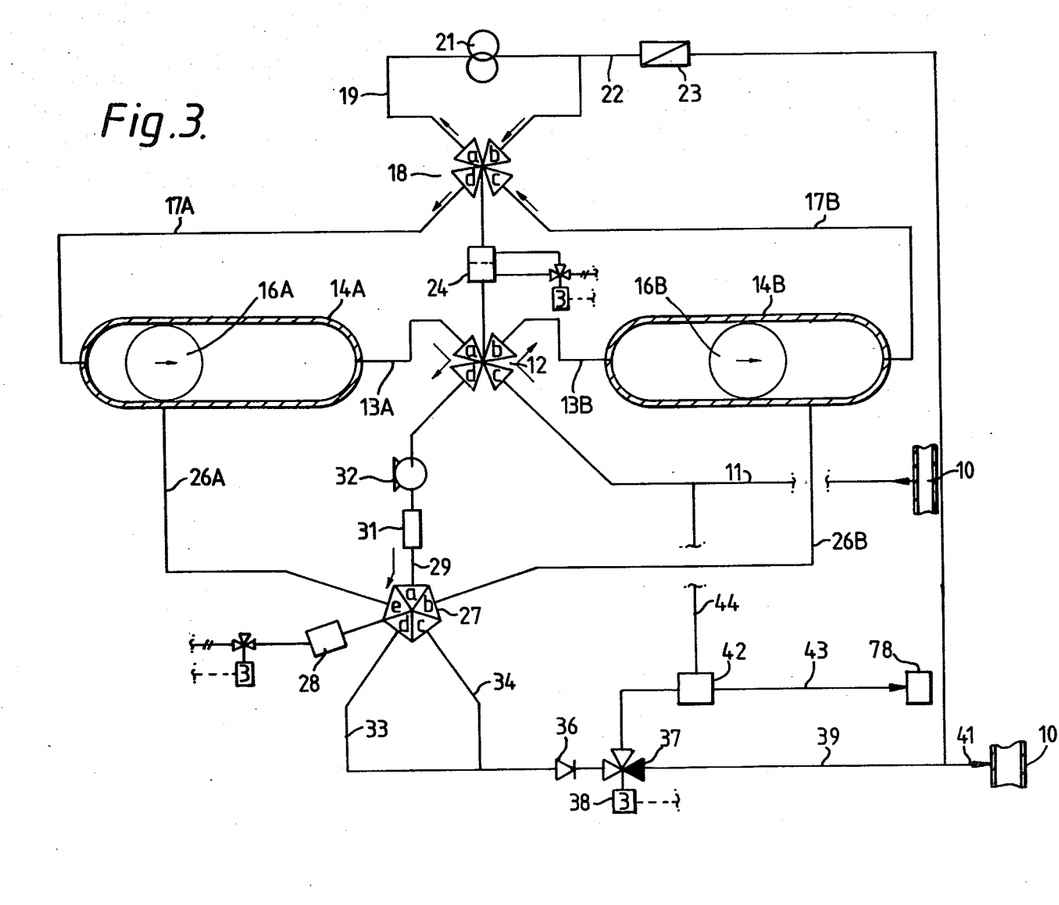
Figure 4:
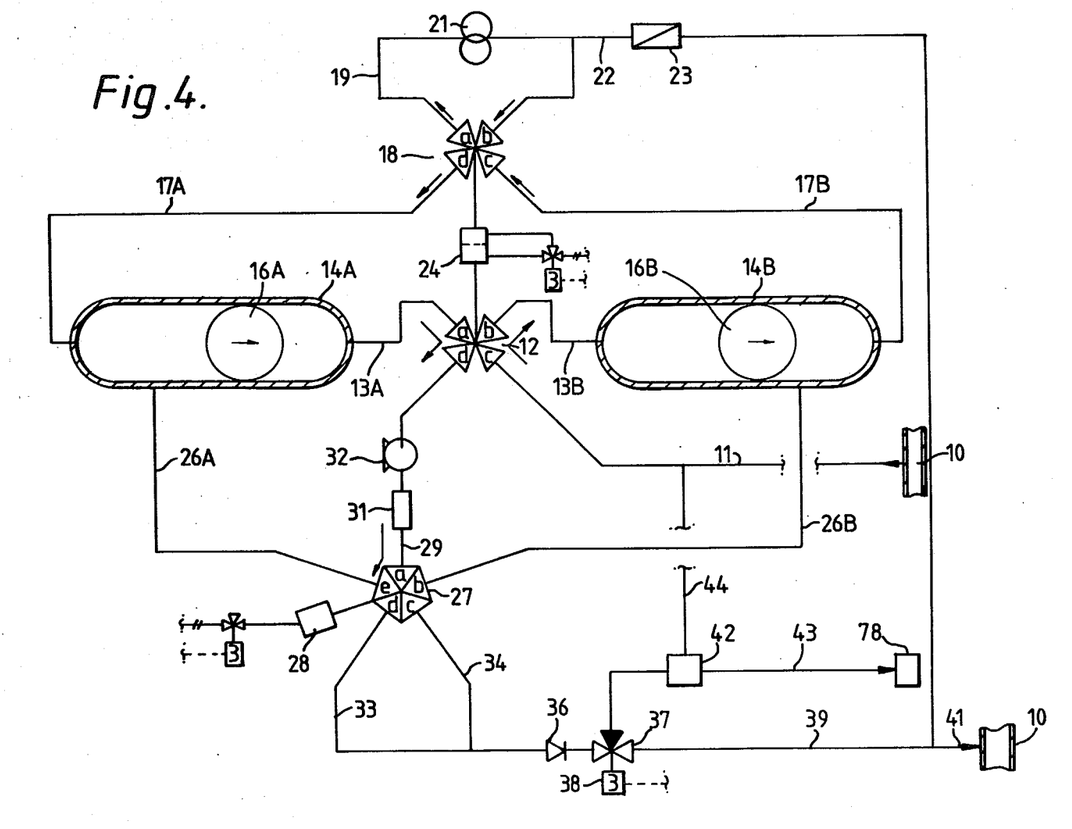

When the ball 16A reaches or is adjacent the left hand end (as viewed in FIG. 1) of the vessel 14A so that the vessel 14A is substantially full of oil from the pipeline the actuator 24 is actuated so as to rotate both the valves 12 and 18. This is illustrated in FIG. 2 and as can be seen the line 17B is now connected to the line 19 in place of the line 17A and the inlet line 11 is now connected through the line 13B to the second vessel 14B. Thus oil from the pipeline is withdrawn and passed into the second vessel 14B in the same manner as described before for vessel 14A so that the ball 16B moves to the right in vessel 14B. Oil is thus withdrawn from the pipeline continuously. There is now present therefore in the vessel 14A a predetermined quantity of oil which has been withdrawn from the pipeline over a period of time and it is desired to withdraw a sample from this volume. Before doing so, however, it is important that the withdrawn oil should be homogenized and this is carried out in the following manner. It will be noted that in the position of the valve 12 shown in FIG. 2 the line 13A is connected to the line 29 and in valve 27 the line 29 is connected with the line 26A. The positive displacement pump 32 is then operated and oil from within the vessel 14A to the right hand side of the ball 16A is circulated through the vessel 14A, line 13A, pump 32, mixer 31 and line 26A. It has been found in practice that within a few minutes the oil has been homogenised. The valve 27 may then be actuated so as to connect the line 29 with either the line 33 or 34 and the oil within the vessel 14A is then pumped out by the positive displacement pump from the vessel through the valve 37 to the probe return 41 (see FIG. 3) However, for a predetermined period during the passage of the oil through the valve 37 the valve 37 is actuated so as to pass a small sample to the back pressure regulator 42 and hence to the output sample line 43. The back pressure regulator ensures that the system is pressure balanced. The amount of oil that is withdrawn as a sample can be varied by varying the period during which the valve 37 is switched to pass oil to the regulator 42 rather than to the probe return 41. Because of the mixing process the sample is an accurate sample of the oil which has been withdrawn from the pipeline during the period the vessel 14A was filling.

Figure 5:
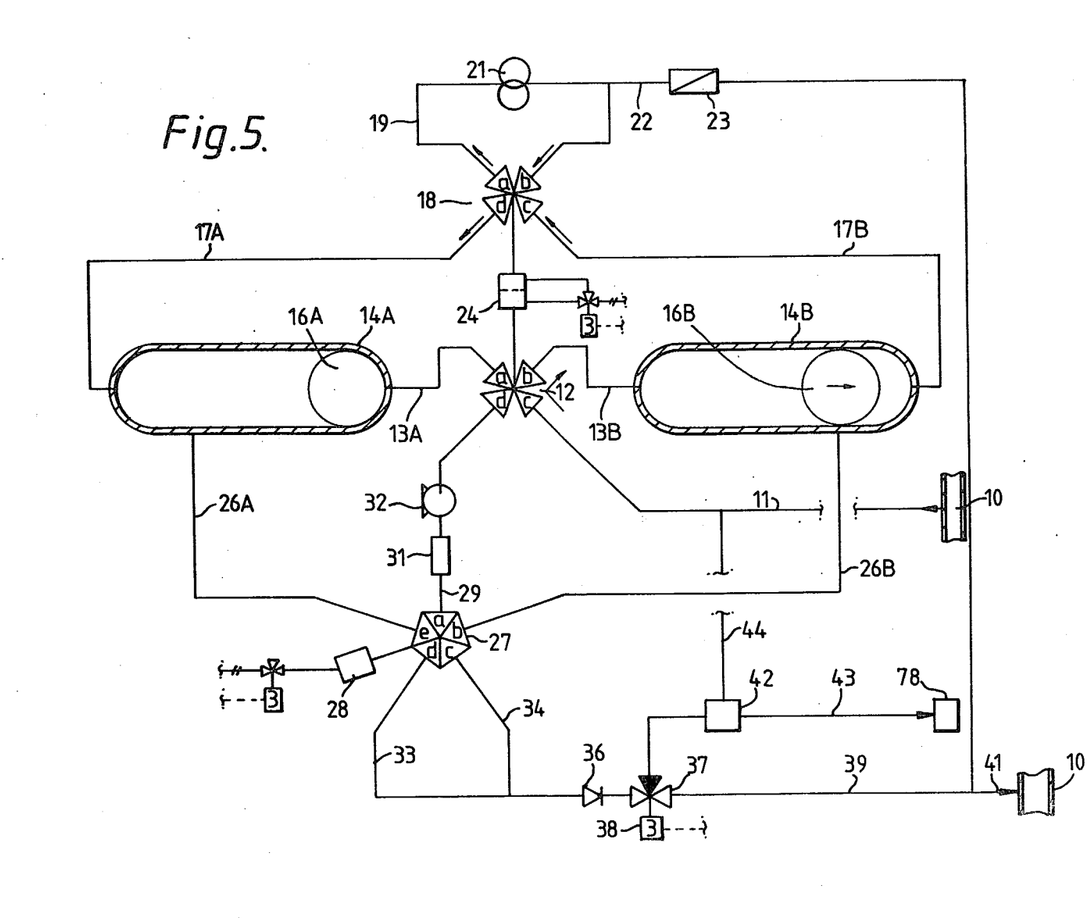

The time taken to empty the vessel 14A, that is for the ball 16A to move to the right hand side is less than that time taken to fill the second vessel 14B and so the ball 16A moves to the right hand side of the vessel 14A before the vessel 14B is full and this situation is shown in FIG. 5.

Furthermore, it will be understood that whilst the ball 16A is moving to the right the left hand side of the vessel 14A is being filled by oil from the downstream side of the gear pump 21 via line 22, valve 18 and line 17A.

When the vessel 14B is full of oil from the pipeline the valving is switched so as to begin filling the vessel 14A with fresh pipeline oil and the process is repeated. Whilst the vessel 14A is being filled oil from the vessel 14B is passed through line 13B, pump 32, mixer 31, line 26B for mixing and thereafter by switching the valve 27 is passed along line 34 through the valve 37 whereby a sample may be taken of the oil collected in the vessel 14B. The process may be repeated back and forth alternately filling each of the vessels 14A, 14B, and whilst one vessel is filling. the oil in the other vessel is being mixed and a sample taken.

In a preferred arrangement, by means of having a probe inlet of approximately 4 mm diameter and vessels of approximately 30 liters capacity it takes approximately half an hour to fill each vessel.

The apparatus can operate at high pressures, for example, up to 1500 psi and can operate on high vapour pressure crude oil.

Figure 6:
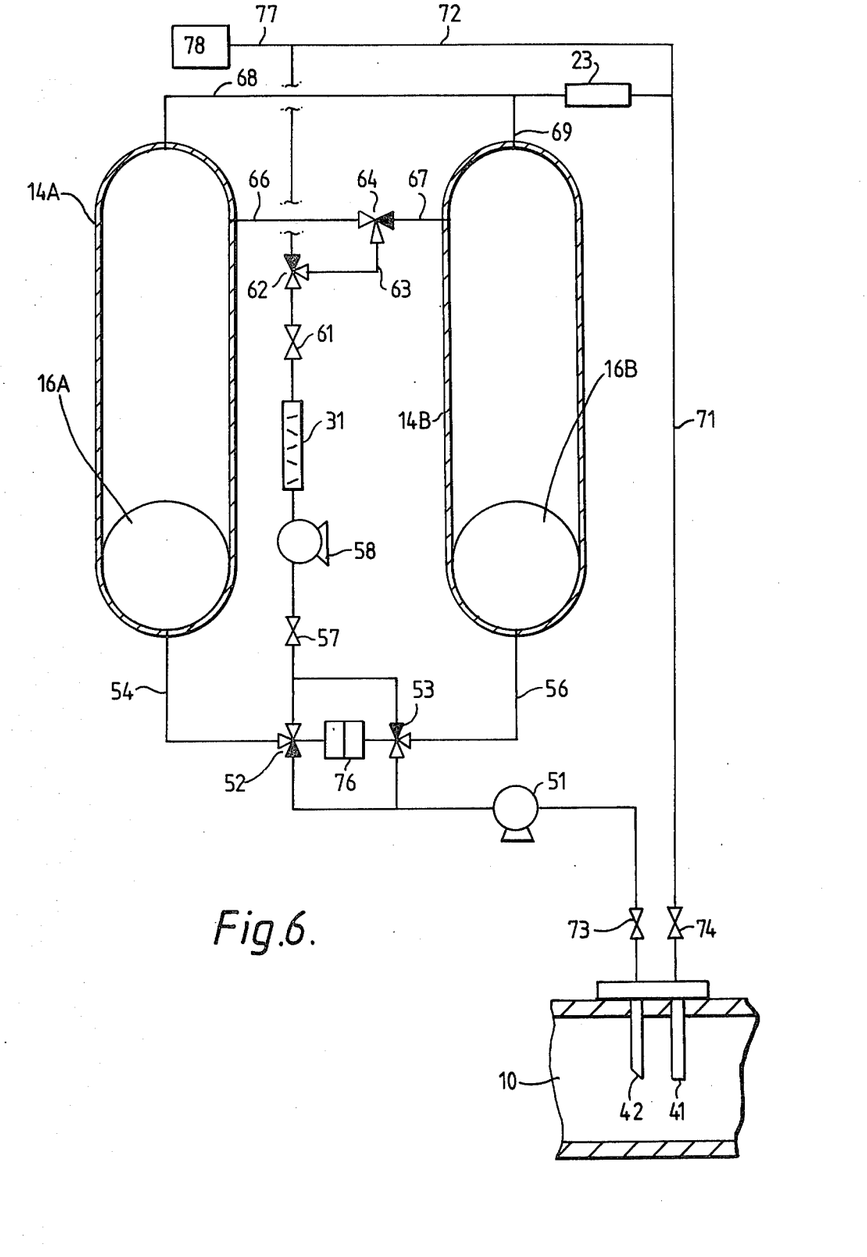
FIGS. 6 to 10 show a second embodiment of the apparatus of the invention in diagramatic form at various stages through the method of invention.

The second arrangement of the invention is shown in FIGS. 6 to 10. In the arrangement of FIG. 6 there is shown a pipeline 10, an inlet line 11, a first pressure vessel 14A and a second pressure vessel 14B, including balls 16A, 16B, a filter 23, mixer 31, sampler 78 probe inlet and a probe return 41. The above parts are similar to those shown in the first arrangement of the invention with respect to FIGS. 1 to 5. The input line 11 is connected to a metering pump 51, arranged so as to be able to pass up to 9 liters per minute. The output of the metering pump 51 is connected to two two-way valves 52 and 53, one outlet of the valve 52 being connected by line 54 to a first end of vessel 14A and one outlet of the valve 53 being connected by line 56 to a first end of vessel 14B. The other outlets of the valves 52 and 53 are each connected to a line valve 57. The line valve 57 is in turn connected to a mixing pump 58 which is arranged to operate at 30 liters per minute, the mixing pump 58 being connected to the mixer 31. The mixer 31 is connected through line valve 61 to a two-way valve 62. One of the other two connections of the valve 62 is connected by line 63 to a two-way valve 64, the two-way valve 64 having outlets connected respectively to pressure vessels 14A and 14B by lines 66 and 67, the lines 66 and 67 connecting with the pressure vessels 14A and 14B at their second ends. The actual points at which the lines 66 and 67 enter the vessels 14A and 14B is slightly towards the centre of the respective pressure vessel with respect to the position of the diameter of the respective ball 16A and 16B when situated at that second end of the pressure vessel 14A and 14B. The filter 23 is connected by lines 68 and 69 with the second ends of pressure vessels 14A and 14B and the opposite side of filter 23 is connected to both the probe return 41 by line 71 and the valve 62 by line 72. A line 77 connects line 72 to sampler 78.

The apparatus can be isolated from the probe inlet 42 and probe return 41 by means of the isolator valves 73 and 74 in lines 11 and 71.

It will also be understood that the valves 52 and 53 are rotated together by means of a common drive means 76 which may be electric or pneumatic.

Figure 7:
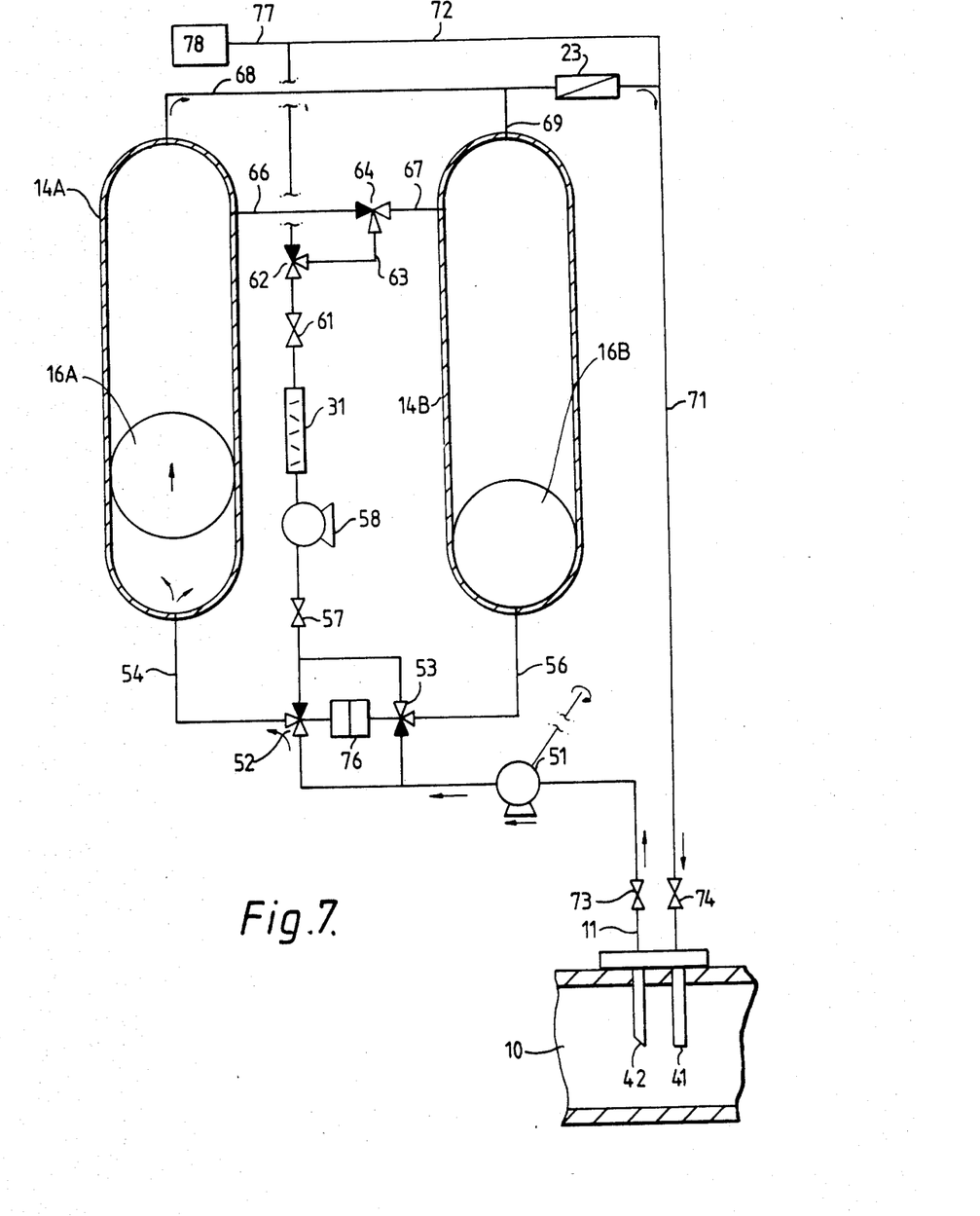
Figure 8:
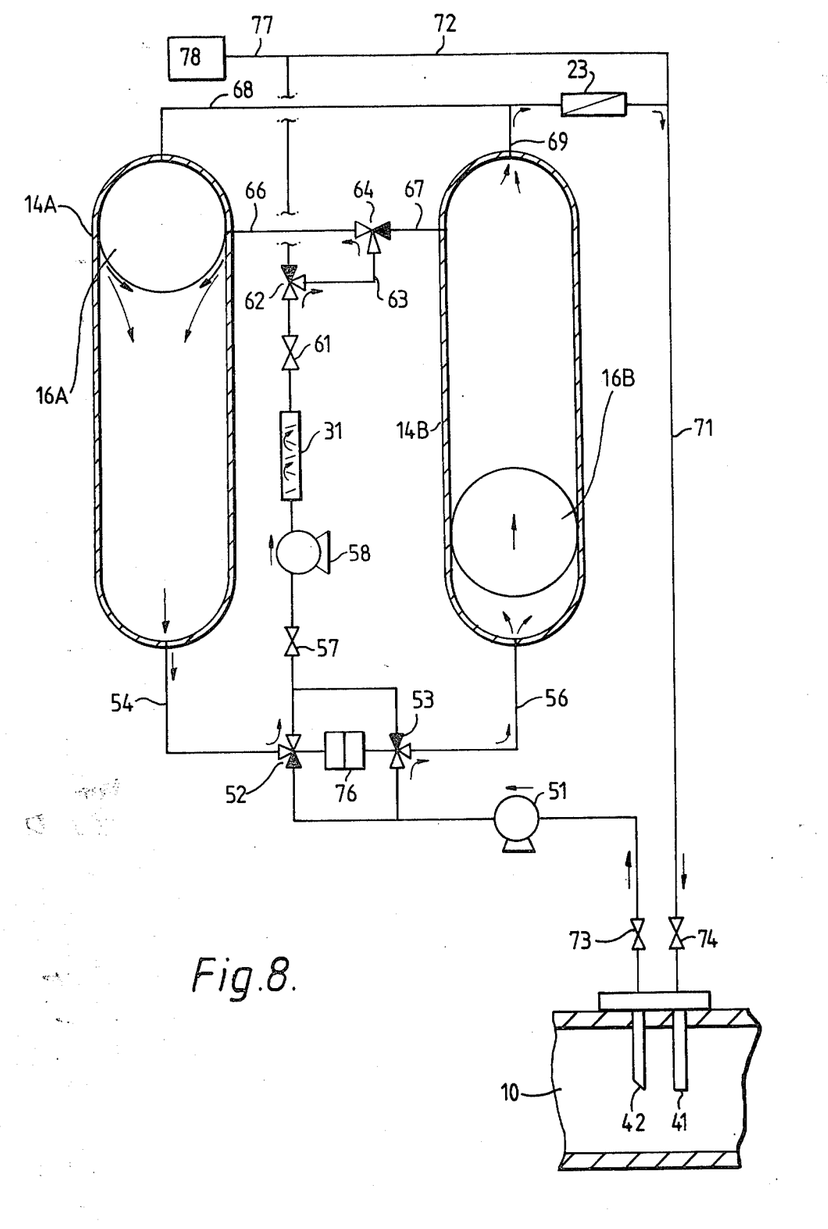
Figure 9:
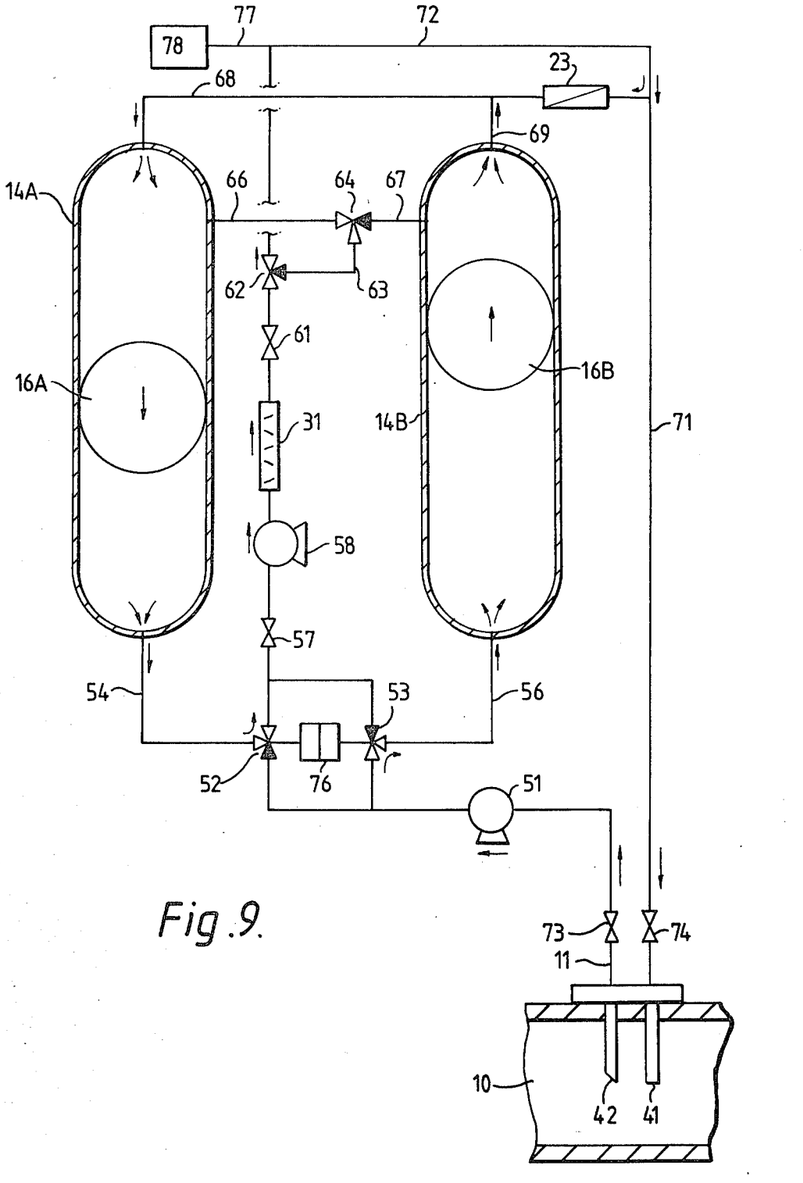

The apparatus described with respect to FIGS. 6 to 10 is operated in the following way. FIG. 6 shows the position before operation. The balls 16A and 16B are adjacent the first end of the respective vessels 14A and 14B. The metering pump 51 is switched off and the valves 52 and 53, 62 and 64 are in a position as shown. The valves 52, 53, 62 and 64 are then switched to the position shown in FIG. 7, the metering pump 51 is switched on and the liquid is isokinetically withdrawn from the pipeline 10 through the probe inlet 42 to the line 11 at a metered rate by the pump 51. The withdrawn fluid passes through valve 52 to line 54 and then into the first end of the pressure vessel 14A. As is clear from FIG. 6 and FIG. 7, the ball 16A is resident at the first end of the vessel 14A. The metering of the fluid into the lower end of the vessel 14A causes the ball 16A to be pushed towards the second end of the vessel 14A as is shown in FIG. 8. In that position, the drive means 76 operates to change the valve 52 and 53 to the opposite configuration that is, to connect the metering pump 51 to line 56 so that fluid withdrawn through the inlet probe 42 is passed to the first end of the vessel 14B to cause the ball 16B to move from the first end to the second end of vessel 14B.

At the same time valve 52 interconnects the mixing pump 58 with the line 54, and the mixing pump is therefore switched on. Fluid is then withdrawn from the first end of the vessel 14A through the line 54 through the mixing pump 58 and through the mixer 31. The fluid then passes through the valve 62 to the line 63, through the valve 64 to the line 66 as indicated by the arrows and is reinserted into the vessel 14A at a position, as is clear from FIG. 8, below the diameter of the ball 16A. The mixing of the fluid in the vessel 14A is accomplished by means of the mixer as was described with reference to the previous embodiment. The mixing is in fact completed before the ball 16B reaches the second end of the vessel 14B, and when the mixing has been completed the valve 62 is changed to its alternate position in which the mixer 31 is connected with the line 72 and hence by line 77 with the sampler 78. In this way the sampler 78 samples the mixed liquid from the vessel 14A and so samples an average fluid received over the period of time during which the vessel 14A was filled. The remaining fluid from vessel 14A passes through line 72 and filter 23 to the second end of the vessel 14A, it being understood therefore, that the operation of the mixing pump 58 actually provides the energy to move the ball 16A from the second end to the first end of the vessel 14A. This operation is shown clearly in FIG. 9.

Figure 10:
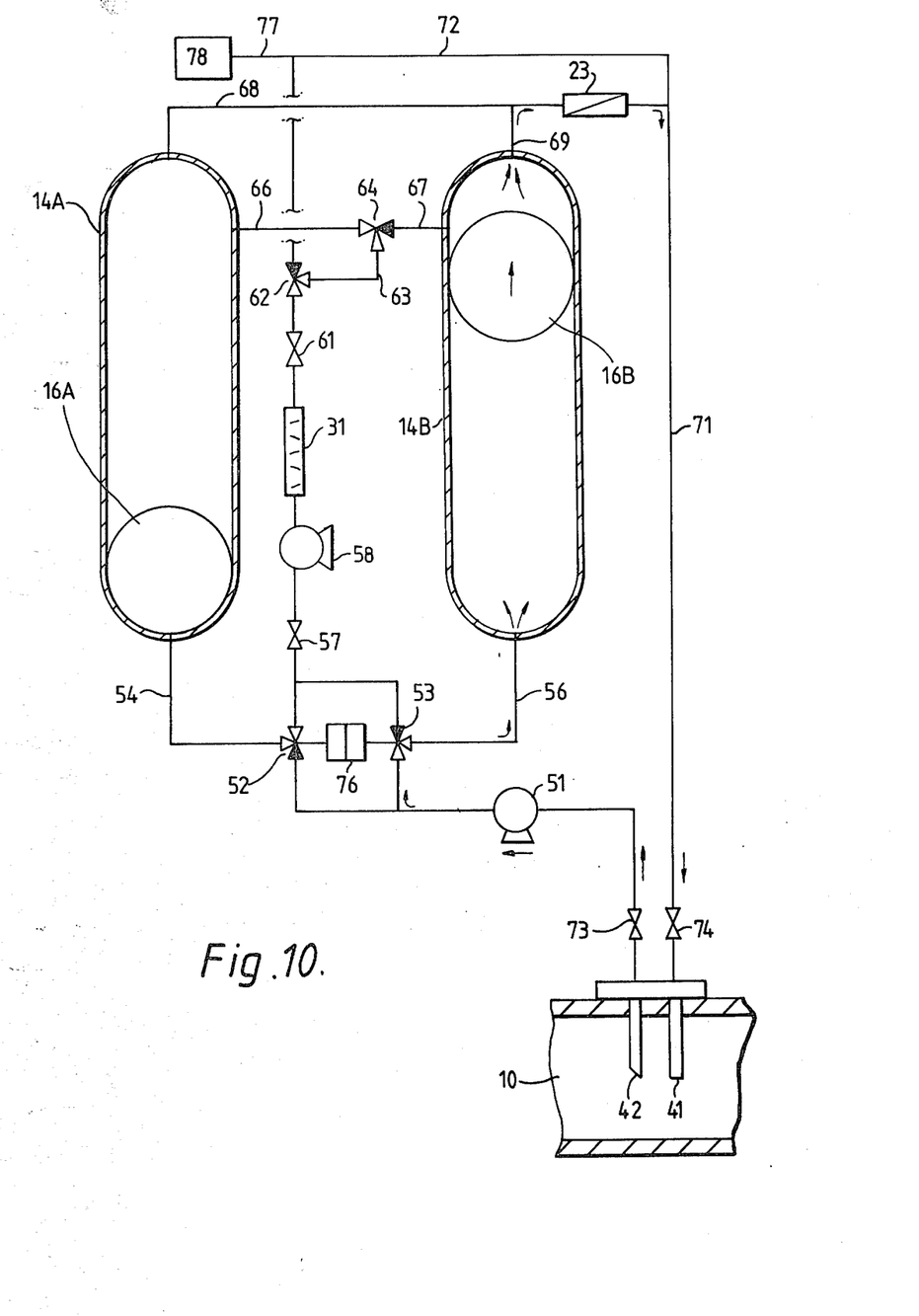

It is clear from FIG. 10 that the ball 16A reaches the first end of the vessel 14A before the ball 16B reaches the second end of the vessel 14B. At this point the mixing pump 58 is switched off. When the ball 16B reaches the second end of the vessel 14B then the valves 52 and 53, 62 and 64 are switched to the configuration as shown in FIG. 7, the mixing pump 58 is switched on, and the liquid in the vessel 14B is mixed as was described earlier with reference to the liquid in vessel 14A. Indeed the cycle is repeated with respect to vessel 14B in the same way as has already been described with respect to vessel 14A. In the meantime, the liquid withdrawn from the pipeline 10 is pumped by the metering pump 51 to the first end of the vessel 14A which causes the ball 16A to move toward the second end thereof. The liquid which is contained in the second end of the vessel 14A, that is, above the ball 16A, when viewed in FIG. 6, is pushed into the line 68 through the filter 23 and into the line 71 and hence back to the pipeline 10.

The remainder of the cycle will be apparent from the above, but clearly the remainder of the fluid in the second end of the vessel 14B is exhausted through line 69, filter 23 and line 71 to the pipeline 10 when the first end of the vessel 14B is being filled from the pipeline 10.

The dimensions and rate of operation of the apparatus is as follows. Each vessel 14A and 14B is approximately 30 liters capacity, is of 8 inch diameter (approx. 20 cm). The time to fill each vessel will depend upon the speed at which the metering pump is operating but is normally between 15 and 30 minutes and the mixing cycle time is approximately 5 minutes. The discharge time, that is the time for the ball to pass from the second end to the first end of the vessel is approximately 1 minute.

I claim:

1. Apparatus for continuously withdrawing a fluid from a source of fluid, comprising:
    two collection apparatus operable alternately to collect part of the fluid;
    fluid mixing means connectable alternately to the two collection apparatus to mix the fluid collected in one of the collection apparatus whilst the other collection apparatus is connected to collect fluid, said fluid mixing means including a pump means for withdrawing fluid from one of the collection apparatus and passing the withdrawn fluid through a mixer such that the withdrawn fluid is passed back to the one of the collection apparatus and passes through the one of the collection apparatus during mixing; and means for sampling a predetermined quantity of the mixed fluid.

2. Apparatus as claimed in claim 1 in which each collection apparatus comprises a substantially identical vessel having a movable wall means.

3. Apparatus claimed in claim 2 in which the vessels are generally cylindrical and the movable wall means each comprise a ball sealingly engaging the cylindrical inner wall of the respective vessel.

4. Apparatus as claimed in claim 2 in which a second pump means is provided to pump fluid from the source of fluid and means is provided to pass the pumped fluid to the vessels alternately.

5. Apparatus as claimed in claim 4 in which the second pump means comprises a controlled metering pump.

6. Apparatus as claimed in claim 1 in which withdrawal means is provided to connect said two collection apparatus to said source of fluid, said withdrawal means being connected to valve means to connect said withdrawal means alternately to said two collection apparatus, second valve means being provided to selectively connect alternately said two collection apparatus to the fluid mixing means, and third valve means arranged to alternately connect said two collection apparatus to means for returning said fluid to the source of fluid.

7. A method for continuously withdrawing a fluid from a fluid supply comprising:
   alternately withdrawing the fluid from the fluid supply to two separate containers;
   and whilst one container is being filled, mixing the fluid in the second container by withdrawing the fluid from said second container and passing the fluid through a mixer and then returning the fluid to said second container;
   sampling the mixed fluid; and
   withdrawing said fluid from said second container.

8. A method as claimed in claim 7 in which the fluid is withdrawn from the fluid supply isokinetically.

9. A method as claimed in claim 7 in which the fluid from the fluid supply is pumped into said containers alternately.

10. A method as claimed in claim 7 in which the fluid in said containers is alternately withdrawn by a pump to withdraw fluid from the source of fluid.

11. An oil pipeline apparatus for withdrawing oil from a pipeline, said apparatus comprising:
    withdrawal means connectable to the pipeline for withdrawing oil form the pipeline;
    first and second collection apparatus operable alternately to collect a proportion of the oil withdrawn from the pipeline;
    fluid mixing means connectable alternately to the two collection apparatus to mix the fluid collected in one of the collection apparatus whilst the other collection apparatus is collecting oil from the pipeline, said fluid mixing means including a pump means for withdrawing fluid from one of the collection apparatus and passing the withdrawn fluid through a mixer such that the withdrawn fluid is passed back to the one of the collection apparatus and passes through the one of the collection apparatus during mixing;
    means for sampling a predetermined quantity of the mixed oil; and
    means for returning the remainder of the mixed oil to the pipeline.

12. An apparatus for continuously withdrawing a fluid from a source of fluid, said apparatus comprising:
    two collection apparatus for alternately collecting some of the fluid, each collection apparatus including a vessel having a moveable wall and being connectable to the source of the fluid;
    fluid mixing means, alternately connectable to said two collection apparatus, for mixing the collected fluid in one of said two collection apparatus while the other collection apparatus is collecting fluid from the source of fluid, said fluid mixing means including a pump means for withdrawing fluid from one of the collection apparatus and passing the withdrawn fluid through a mixer such that the withdrawn fluid is passed back to the one of the collection apparatus and passes through the one of the collection apparatus during mixing;
    means for sampling a predetermined quantity of the mixed fluid;
    second pump means for pumping the mixed fluid out of one of the vessels; and
    connecting means, operatively connected between said second pump means and each of said vessels, for alternately connecting said second pump means to one of said vessels so that as fluid is pumped out of said one of said vessels, said movable wall of said one of said vessels is moved and fluid is withdrawn from said source of fluid into said one of said vessels.

13. Apparatus for continuously withdrawing a fluid from a source of fluid, according to claim 12, wherein the second pump means comprises a controlled metering pump.

* * * * *